United States Patent [19]
Pall et al.

[11] Patent Number: 5,316,674
[45] Date of Patent: * May 31, 1994

[54] DEVICE FOR PROCESSING BLOOD FOR HUMAN TRANSFUSION

[75] Inventors: David B. Pall; Thomas C. Gsell, both of Glen Cove; Brian T. Muellers, Rockville Centre, all of N.Y.

[73] Assignee: Pall Corporation, Glen Cove, N.Y.

[*] Notice: The portion of the term of this patent subsequent to Mar. 31, 2009 has been disclaimed.

[21] Appl. No.: 933,309

[22] Filed: Aug. 21, 1992

Related U.S. Application Data

[63] Continuation of Ser. No. 609,574, Nov. 6, 1990, Pat. No. 5,152,905, which is a continuation-in-part of Ser. No. 405,977, Sep. 12, 1989, abandoned.

[51] Int. Cl.$^5$ .................. B01D 29/00; B01D 35/00
[52] U.S. Cl. .................. 210/257.1; 210/505; 210/508; 604/406
[58] Field of Search .............. 210/257.1, 295, 314, 210/323.1, 348, 435, 496, 767, 806, 505, 508; 604/4, 5, 6, 406; 422/44, 101

[56] References Cited

U.S. PATENT DOCUMENTS

| | | | |
|---|---|---|---|
| 4,596,657 | 6/1986 | Wisdom | 210/206 |
| 4,880,548 | 11/1989 | Pall et al. | 210/508 |
| 5,100,564 | 3/1992 | Pall et al. | 210/806 |
| 5,152,905 | 10/1992 | Pall et al. | 210/767 |

FOREIGN PATENT DOCUMENTS 0267286  5/1988  European Pat. Off.

Primary Examiner—Robert A. Dawson
Assistant Examiner—Sun U. Kim
Attorney, Agent, or Firm—Leydig, Voit & Mayer

[57] ABSTRACT

A device for processing donated blood comprises a porous medium interposed between the collection bag and a satellite bag into which a component separated by centrifugation can be expressed, the filter element preferably having a CWST of about 70 to about 115 dynes/cm. The porous medium blocks red blood cells, but allows platelets to pass therethrough.

9 Claims, 2 Drawing Sheets 5,316,674

DEVICE FOR PROCESSING BLOOD FOR HUMAN TRANSFUSION

This application is a continuation of application Ser. No. 07/609,574, filed Nov. 6, 1990, now U.S. Pat. No. 5,152,905, which is a continuation-in-part of application Ser. No. 07/405,977, filed Sep. 12, 1989 and now abandoned.

TECHNICAL FIELD

This invention relates to a method and apparatus for processing blood donated for the purpose of therapeutic transfusion of blood components and, particularly, to improved methods and apparatuses for preparing, from the donated whole blood, leucocyte depleted platelet-rich plasma (hereinafter PRP), platelet concentrate (hereinafter PC), and plasma.

BACKGROUND OF THE INVENTION

The development of plastic blood collection bags facilitated the separation of donated whole blood into its various components, thereby making platelet concentrates available as a transfusion product. The separation of a single unit of donated whole blood, about 450 milliliter in USA practice, into its components is typically accomplished by use of differential sedimentation.

A typical procedure used in the United States, the citrate-phosphate-dextrose-adenine (CPDA-1) system, utilizes a series cf steps to separate donated blood into three components, each component having substantial therapeutic and monetary value. The procedure typically utilizes a blood collection bag which is integrally attached via tubing to at least one, and preferably two or more, satellite bags. Whole blood may be thus collected and processed as follows:

(1) The donated whole blood is collected from the donor's vein directly into the blood collection bag which contains the nutrient and anti-coagulant containing CPDA-1.

(2) The blood collection bag is centrifuged together with its satellite bags, thereby concentrating the red cells as packed red cells (hereinafter PRC) in the lower portion of the blood collection bag and leaving in the upper portion of the bag a suspension of platelets in clear plasma, which is known as platelet-rich plasma (PRP).

(3) The blood collection bag is transferred, with care not to disturb the interface between the supernatant PRP layer and the sedimented PRC layer, into a device known as a "plasma extractor" which comprises an opaque back plate and a transparent front plate; the two plates are hinged together at their lower ends and spring biased toward each other such that a pressure of about 90 millimeters of mercury is developed within the bag. With the blood collection bag positioned between the two plates, a valve or seal in the tubing is opened allowing the supernatant PRP to flow into a first satellite bag. As the PRP flows out of the blood collection bag, the interface with the PRC rises. The operator closely observes the position of the interface as it rises and clamps off the connecting tube when in his judgment as such PRP has been transferred as is possible, consistent with allowing no red cells to enter the first satellite bag. This is a time consuming operation during which the operator must visually monitor the bag and judiciously and arbitrarily ascertain when to shutoff the connecting tube. The blood collection bag, now containing only PRC, may be detached and stored at 4° C. until required for transfusion into a patient, or a valve or seal in the flexible tubing may be opened so that the PRC may be transferred to a satellite bag using either the pressure generated by the plasma extractor apparatus, or by placing the blood collection apparatus in a pressure cuff, or by elevation to obtain gravity flow.

(4) The PRP-containing satellite bag, together with another satellite bag, is then removed from the extractor and centrifuged at an elevated G force with the time and speed adjusted so as to concentrate the platelets into the lower portion of the PRP bag. When centrifugation is complete, the PRP bag contains sedimented platelets in its lower portion and clear plasma in its upper portion.

(5) The PRP bag is then placed in the plasma extractor, and most of the clear plasma is expressed into the other satellite bag, leaving the PRP bag containing only sedimented platelets in about 50 ml of plasma; in a subsequent step, this platelet composition is dispersed to make PC. The PRP bag, now containing a PC product, is then detached and stored for up to five days at 20°-22° C., until needed for a transfusion of platelets. For use with adult patients, the platelets from 6–10 donors are, when required, pooled into a single platelet transfusion.

(6) The plasma in the other satellite bag may itself be transfused into a patient, or it may be separated by complex processes into a variety of valuable products.

Commonly used systems other than CPDA-1 include Adsol, Nutricell, and SAG-M. In these latter systems, the collection bag contains only anti-coagulant, and the nutrient solution may be preplaced in a satellite bag. This nutrient solution is transferred into the PRC after the PRP has been separated from the PRC, thereby achieving a higher yield of plasma and longer storage life for the PRC.

With the passage of time and accumulation of research and clinical data, transfusion practices have changed greatly. One aspect of current practice is that whole blood is rarely administered; rather, patients needing red blood cells are given packed red cells, patients needing platelets are given platelet concentrate, and patients needing plasma are given plasma.

For this reason, the separation of blood into components has substantial therapeutic and monetary value. This is nowhere more evident than in treating the increased damage to a patient's immune system caused by the higher doses and stronger drugs now used during chemotherapy for cancer patients. These more aggressive chemotherapy protocols are directly implicated in the reduction of the platelet content of the blood to abnormally low levels; associated internal and external bleeding additionally requires more frequent transfusions of PC, and this has caused platelets to be in short supply and has put pressure on blood banks to increase platelet yield per unit of blood.

Blood bank personnel have responded to the increased need for blood components by attempting to increase PC yield in a variety of ways, including attempting to express more PRP prior to stopping flow from the blood collection bag. This has often proved to be counterproductive in that the PRP, and the PC subsequently extracted from it, are not infrequently contaminated by red cells, giving a pink or red color to the normally light yellow PC. The presence of red cells in PC is so highly undesirable that pink or red PC is frequently discarded, or subjected to recentrifugation, both of which increase operating costs.

The devices and methods of this invention alleviate the above-described problems and, in addition, provide a higher yield of superior quality PC.

In addition to the three above-listed components, whole blood contains white blood cells (known collectively as leucocytes) of various types, of which the most important are granulocytes and lymphocytes. White blood cells provide protection against bacterial and viral infection.

LEUCOCYTE DEPLETION OF PLATELET SUSPENSIONS

The transfusion of blood components which have not been leuco-depleted is not without risk to the patient receiving the transfusion. Chills, fever, and allergic reactions may occur in patients receiving acute as well as chronic platelet therapy. Repeated platelet transfusions frequently lead to alloimmunization against HLA antigens, as well as platelet specific antigens. This, in turn, decreases responsiveness to platelet transfusion. Leucocytes contaminating platelet concentrates, including granulocytes and lymphocytes, are associated with both febrile reactions and alloimmunization, leading to platelet transfusion refractoriness. Another life-threatening phenomenon affecting heavily immunosuppressed patients is Graft Versus Host Disease. In this clinical syndrome, donor lymphocytes transfused with the platelet preparations can launch an immunological reaction against the transfusion recipient with pathological consequences. Some of these risks are detailed in U.S. Pat. No. 4,923,620, incorporated herein by reference, and in U.S. Pat. No. 4,880,548, also incorporated herein by reference.

In the above described centrifugal method for separating blood into the three basic fractions, the leucocytes are present in substantial quantities in both the packed red cells and platelet-rich plasma fractions. It is now generally accepted that it would be highly desirable to reduce the leucocyte concentration of these blood components to as low a level as possible. While there is no firm criterion, it is generally accepted that many of the undesirable effects of transfusion would be reduced if the leucocyte content were reduced by a factor of about 100 or more prior to administration to the patient. This approximates reducing the average total content of leucocytes in a single unit of PRC or PRP to less than about $1 \times 10^7$, and in a unit of PRP or PC to less than about $1 \times 10^6$.

Growing evidence suggests that the use of leucocyte depleted platelet concentrates decreases the incidence of febrile reactions and platelet refractoriness. Leucocyte depleted blood components are also believed to have a role in reducing the potential for Graft Versus Host Disease. Leucocyte depletion of platelet preparations is also believed to diminish, but not to completely prevent, the transmission of leucocyte associated viruses such as HIV-1 and CMV.

Platelet preparations contain varying amounts of leucocytes. The level of leucocyte contamination in unfiltered conventional platelet preparations of 6 to 10 pooled units is generally at a level of about $5 \times 10^8$ or greater. Platelet concentrates prepared by the differential centrifugation of blood components will have varying levels of leucocyte contamination related to the time and to the magnitude of the force developed during centrifugation. It has been demonstrated that leucocyte removal efficiencies of 81 to 85% are sufficient to reduce the incidence of febrile reactions to platelet transfusions. Several other recent studies report a reduction in alloimmunization and platelet refractoriness at levels of leucocyte contamination $<1 \times 10^7$ per unit. For a single unit of PC averaging a leucocyte contamination level (under current practice) of about $7 \times 10^7$ leucocytes, the goal after filtration is less than $1 \times 10^6$ leucocytes. The existing studies therefore suggest the desirability of at least a two log (99%) reduction of leucocyte contamination. More recent studies suggest that a three log (99.9%) or even a four log (99.99%) reduction would be significantly more beneficial.

An additional desirable criterion is to restrict platelet loss to about 15% or less of the original platelet concentration. Platelets are notorious for being "sticky", an expression reflecting the tendency of platelets suspended in blood plasma to adhere to any non-physiological surface to which they are exposed. Under many circumstances, they also adhere strongly to each other.

In any system which depends upon filtration to remove leucocytes from a platelet suspension, there will be substantial contact between platelets and the internal surfaces of the filter assembly. The filter assembly must be such that the platelets have minimal adhesion to, and are not significantly adversely affected by contact with, the filter assembly's internal surfaces. Such a filter assembly is an objective of this invention.

U.S. Pat. No. 4,880,548 (hereinafter '548) provides a convenient and very effective means for leuco-depleting PC. PC is passed through a fibrous filter which permits recovery of 90% or more of the platelets, which pass through the filter, while retaining within the filter more than 99.9% of the incident leucocytes. This system is currently in widespread use at bedside in hospitals, but, unlike the device of this invention, it is not well suited for use in blood banks during the processing of donated blood. The unsuitability stems primarily from additional storage constraints associated with PC and the methods of administering PC. For example, platelets in PC are typically suspended in a total volume of only about 40 to 60 ml of plasma. Contrasted with this, the platelets which are processed by the devices and methods of this invention are derived from a single unit of whole blood and are suspended as PRP in about 180 to 240 ml of plasma. Further, the platelets in PC have been subjected during centrifugation to severe conditions and there is reason to believe that, as a result of the high forces to which the platelets are subjected as they reach the bottom of the bag during sedimentation, they are not as readily dispersed, i.e., they are more aggregated by particle-to-particle adhesion, when compared with the platelet distribution in PRP.

For these and perhaps other reasons, platelets in PC show a much higher tendency to be retained within the filter during leuco-depletion compared with platelets in PRP. Indeed, one of the advantages of the devices and methods of this invention is that much better recovery is obtained when platelets are leuco-depleted in the form of PRP, compared with PC; for example, while optimal recovery from PC is about 90 to 95%, recovery from PRP can exceed 99%.

Also, as a consequence of the concentration differences and possibly as a consequence of the lower degree of aggregation in PRP, the preferred critical wetting surface tension (CWST) range when filtering PRP is broader than those for PC.

Devices which have previously been developed in attempts to meet the above-noted objectives have been based on the use of packed fibers, and have generally been referred to as filters. However, it would appear that processes utilizing filtration based on separation by size cannot succeed for two reasons. First, leucocytes can be larger than about 15 μm (e.g., granulocytes and macrocytes) to as small as 5 to 7 μm (e.g., lymphocytes). Together, granulocytes and lymphocytes represent the major proportion of all of the leucocytes in normal blood. Red blood cells are about 7 μm in diameter, i.e., they are about the same size as lymphocytes, one of the two major classes of leucocytes which must be removed. Secondly, all of these cells deform so that they are able to pass through much smaller openings than their normal size. Accordingly, it has been widely accepted that removal of leucocytes is accomplished mainly by adsorption on the internal surfaces of porous media, rather than by filtration.

The separation of the various blood components using centrifugation is attended by a number of problems. First, in the separation of platelet-rich plasma from PRC, e.g., step 3 above, it is difficult to efficiently obtain the maximum yield of platelets while preventing red cells from entering the plasma. Secondly, when PRP is centrifuged to obtain a layer consisting principally of platelets concentrated at the bottom of the PRP-containing bag, e.g., step 4 above, the platelets so concentrated tend to form a dense aggregate which must be dispersed in plasma to form platelet concentrate. The dispersion step is usually carried out by gentle mixing, for example, by placing the bag on a moving table which rotates with a precessing tilted motion. This mixing requires several hours, a potentially undesirable delay, and is believed by many researchers to result in a partially aggregated platelet concentrate. It is further believed that the platelets may be damaged by the forces applied during centrifugation.

An ideal device for the leucocyte depletion of PRP would be inexpensive, relatively small, and be capable of rapidly processing blood components obtained from about one unit or more of donated whole blood in, for example, less than about one hour. Ideally, this device would also reduce the leucocyte content to the lowest possible level, while avoiding the problems described above.

SUMMARY OF THE INVENTION

PC is typically prepared from donated blood that has been stored until needed and transfused to the patient at bedside as required. Insofar as leuco-depletion of platelets derived from donated blood has been practiced, it has generally been accomplished just prior to or contemporaneous with the transfusion to the patient.

Figure 2:
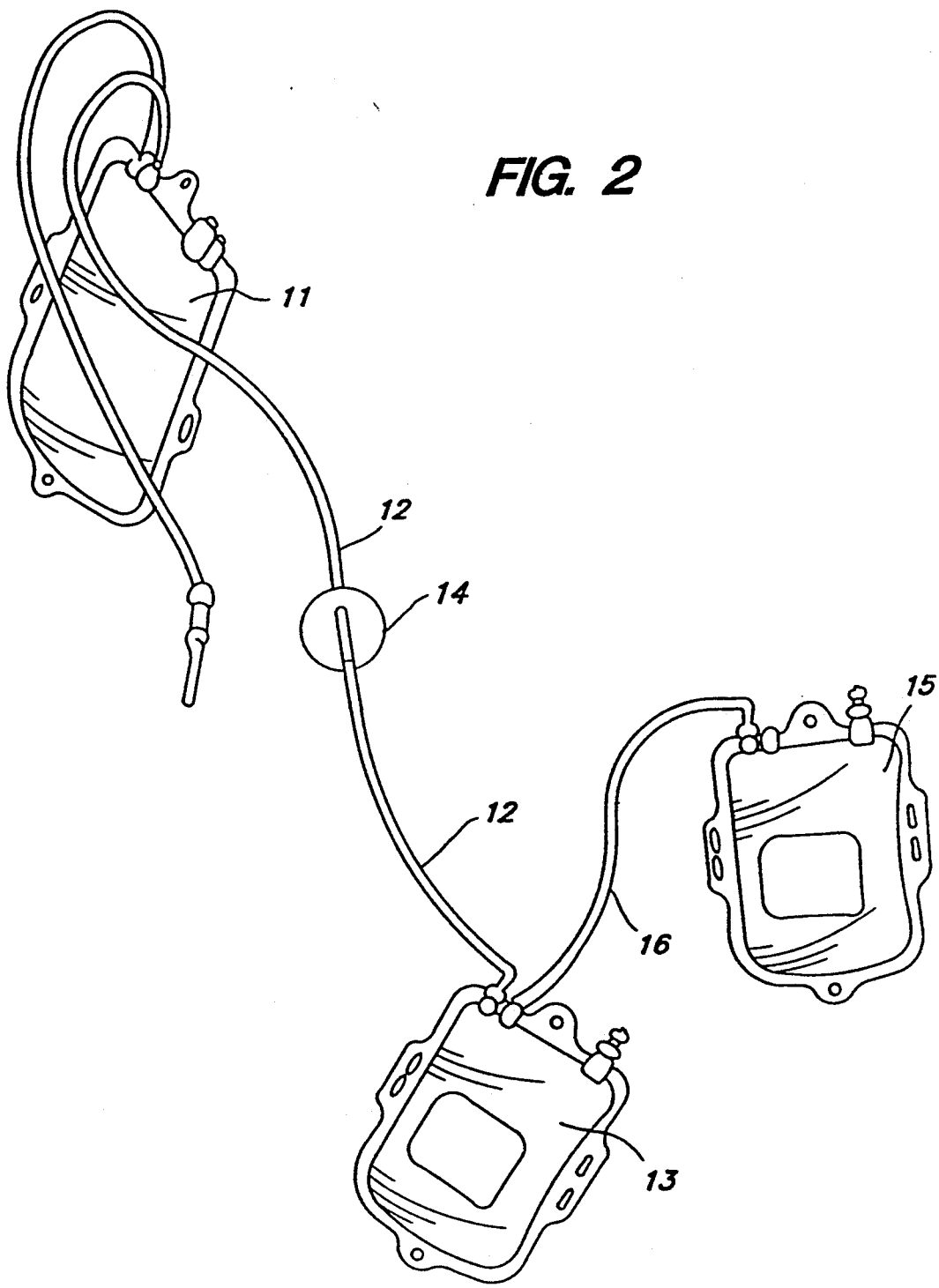
FIG. 2 is identical to FIG. 1 except that tubing 12 has been cut and filter 14 inserted.

In the methods of this invention, leucocyte depletion is preferably accomplished at the time the blood is processed, which in USA practice is within 8 hours of the time the blood was drawn. When PRP is separated from PRC (e.g., step number three of the six step process in a preceding section), the process is modified by interposing a leucocyte depletion filter 14 immediately downstream of the blood collection bag 11 (see FIG. 2). Thus, as the supernatant PRP is expressed by the plasma extractor, leucocytes are removed by the filter and leucocyte-depleted PRP is collected in the satellite bag and is subsequently centrifuged to obtain leucocyte-depleted PC and plasma. In accordance with the invention, an apparatus and method is provided whereby PRP is leucocyte-depleted by interposing between the blood collection bag and a satellite bag at least one porous medium for depleting leucocytes from PRP.

DESCRIPTION OF THE PREFERRED EMBODIMENTS

The present invention involves an apparatus comprising a first container and a second container, and a conduit interconnecting the first container with the second container; and having interposed between the first container and the second container, at least one porous medium including a leucocyte depletion medium, a red cell barrier medium, an assembly comprising a leucocyte depletion medium and a red cell barrier medium, or combinations thereof.

In a preferred form of the filter of the subject invention, the fibers of which the filter element is composed are modified by grafting thereon a mixture of two monomers, one containing hydroxyl groups and another containing anionic groups, such as carboxyl groups, with the hydroxyl groups present in larger numbers. As described in U.S. Pat. No. 4,880,548, herein incorporated by reference, the filter media of this invention are preferably surface modified using a mixture comprising hydroxyl-terminated and carboxyl-terminated monomers. In a preferred form of this invention, the monomers are respectively hydroxyethyl methacrylate (HEMA) and methacrylic acid (MAA), and the monomer ratios are preferably in the range (carboxyl:hydroxyl) of about 0.01:1 to about 0.5:1, and more preferably in the range of about 0.05:1 to about 0.35:1. A preferred monomer ratio is one which produces a desired zeta potential at the pH of plasma (7.3) of about −3 to about −30 millivolts, a more preferred ratio produces a zeta potential of about −7 to about −20 millivolts, and a still more preferred ratio produces a zeta potential of about −10 to about −14 millivolts.

The CWST of the filter elements made with the PBT fibers according to this invention have a CWST as formed of about 50 to about 54 dynes/cm, and most or all other fibers which may be used have a CWST below 55 dynes/cm. Surface grafting using the monomers noted above causes the CWST of the fibers to increase, the exact value obtained being dependent on the ratio of the two monomers. A preferred range for the CWST of the devices of this invention is about 70 to about 115 dynes/cm, a more preferred range is about 90 to about 100 dynes/cm and a still more preferred range is about 93 to about 97 dynes/cm, these ranges being obtained by varying the ratio of carboxyl-terminated and hydroxyl-terminated monomers.

Although the fibers of the porous medium may remain untreated, they are preferably treated to make them even more effective. For example, the fibers may be surface modified to increase the critical wetting surface tension (CWST) of the fibers.

As disclosed in U.S. Pat. No. 4,880,548, the CWST of a porous medium may be determined by individually applying to its surface a series of liquids with surface tensions varying by 2 to 4 dynes/cm and observing the absorption or non-absorption of each liquid over time. The CWST of a porous medium, in units of dynes/cm, is defined as the mean value of the surface tension of the liquid which is absorbed and that of the liquid of neighboring surface tension which is not absorbed within a predetermined amount of time. The absorbed and non-absorbed values depend principally on the surface characteristics of the material from which the porous medium is made and secondarily on the pore size characteristics of the porous medium.

Liquids with surface tensions lower than the CWST of a porous medium will spontaneously wet the medium on contact and, if the medium has through holes, will flow through it readily. Liquids with surface tensions higher than the CWST of the porous medium may not flow at all at low differential pressures and may do so unevenly at sufficiently high differential pressures to force the liquid through the porous medium. In order to achieve adequate priming of a fibrous medium with a liquid such as blood, the fibrous medium preferably has a CWST in the range of about 53 dynes/cm or higher.

The number of carboxyl groups per unit of surface area appears to have an important effect on the adhesion of platelets to fiber surfaces. This effect is reflected in the proportion of platelets recovered in the filter effluent as a fraction of the number present in the platelets prior to filtration. Platelet recovery peaks at the optimum proportion of MAA. The number of carboxyl groups per unit of fiber surface is, over the range of interest of this invention, thought to be close to proportional to the amount of MAA in the monomeric grafting solution.

While the porous media can be produced from any material compatible with blood, practical considerations dictate that consideration be given first to the use of commercially available materials. The porous medium of this invention may be formed, for example, from any synthetic polymer capable of forming fibers and of serving as a substrate for grafting. Preferably, the polymer should be capable of reacting with at least one ethylenically unsaturated monomer under the influence of ionizing radiation without the matrix being significantly or excessively adversely affected by the radiation. Suitable polymers for use as the substrate include, but are not limited to, polyolefins, polyesters, polyamides, polysulfones, acrylics, polyacrylonitriles, polyaramides, polyarylene oxides and sulfides, and polymers and copolymers made from halogenated olefins and unsaturated nitriles. Examples include, but are not limited to, polyvinylidene fluoride, polyethylene, polypropylene, cellulose acetate, and Nylon 6 and 66. Preferred polymers are polyolefins, polyesters, and polyamides. The most preferred polymer is polybutylene terephthalate (PBT).

Surface characteristics of a fiber can be modified by a number of methods, for example, by chemical reaction including wet or dry oxidation, by coating the surface by depositing a polymer thereon, and by grafting reactions which are activated by exposure to an energy source such as heat, a Van der Graff generator, ultraviolet light, or to various other forms of radiation. The preferred method is a grafting reaction using gamma-radiation, for example, from a cobalt source.

Radiation grafting, when carried out under appropriate conditions, has the advantage of considerable flexibility in the choice of reactants, surfaces, and in the methods for activating the required reaction. Gamma-radiation grafting is particularly preferable because the products are very stable and have undetectably low aqueous extractable levels. Furthermore, the ability to prepare synthetic organic fibrous media having a CWST within a desired range is more readily accomplished using a gamma radiation grafting technique.

An exemplary radiation grafting technique employs at least one of a variety of monomers each comprising an ethylene or acrylic moiety and a second group, which can be selected from hydrophilic groups (e.g., —COOH, or —OH). Grafting of the fibrous medium may also be accomplished by compounds containing an ethylenically unsaturated group, such as an acrylic moiety, combined with a hydroxyl group, preferably monomers such as HEMA or acrylic acid. The compounds containing an ethylenically unsaturated group may be combined with a second monomer such as MAA. Use of HEMA as the monomer contributes to a very high CWST. Analogues with similar functional characteristics may also be used to modify the surface characteristics of fibers.

In a first variation of the devices of this invention, the PRP derived from a single unit of about 450 cc of human blood is passed, typically during a flow interval of about 10 to 40 minutes, through a filter comprising grafted fibers, the element of the filter preferably comprising fibers with a surface area in the range of about 0.08 to about 1.0 square meters, and more preferably about 0.1 to about 0.7 square meters, with a voids volume in the range of about 50% to about 89% (i.e., if PBT fiber is used, corresponding to a density of the filter element in the range of about 0.69 g/cc to about 0.15 g/cc), and more preferably about 60% to about 85% (for PBT, about 0.55 g/cc to about 0.21 g/cc). The filter element is preferably of right cylindrical form with the ratio of diameter to thickness preferably in the range of about 7:1 to about 40:1. The range of fiber diameter is preferred to be about 1.0 to about 4 $\mu$m and is more preferred to be in the range of about 2 to about 3 $\mu$m. These parameters can be varied; for example, the diameter of the filter element could be reduced and the thickness of the filter element increased while retaining the same total quantity of fiber, or the fibers could be larger in diameter while increasing the total quantity of fiber, or the fibers could be packed as opposed to preformed into a cylindrical disc. Such variations fall within the purview of this invention.

If desired, flow rate of the PRP through the filter can be regulated to obtain a total flow period of about 10 to about 40 minutes by selecting the appropriate element diameter, element thickness, fiber diameter, and density, and/or by varying the diameter of tube 12 either upstream or downstream of the filter, or both up and downstream. At these flow rates, leucocyte depletion efficiency in excess of about 99.9% may be achieved and even as high as about 99.9995%. These levels of efficiency result in a PC product with substantially less than about $0.1 \times 10^6$ leucocytes per unit of PC compared with the target of less than about $1 \times 10^6$ leucocytes per unit.

The above-described device and its mode of use provide the advantages set forth below, among other advantages.

(a) In the blood bank, the filtration step requires no labor input additional to the current practice, and, in the hospital, the need for bedside filtration is completely eliminated.

(b) The volume of the PRP processed is about five or more times that of the PC which is derived from the PRP. Because the volume processed is larger, loss of PC due to hold up within the filter is only about 1% compared with a loss about five or more times greater when PC is filtered at bedside.

(c) Compared with hospital practice, filtration within the blood bank is generally under better control, as it is performed in relatively larger numbers by personnel trained to the specific task.

(d) It is the belief of some researchers that when PC is stored prior to removal of leucocytes, the platelets are damaged during storage as the leucocytes disintegrate, releasing their components, some of which are highly toxic to human tissues. Removing the leucocytes within a few hours after collection is believed to greatly reduce damage due to this cause.

(e) In the process of tapping the donor's vein, the hypodermic needle cuts a disc of the donor's skin which is transferred into the collected blood. The alcohol swab applied prior to venipuncture is not adequate to assure sterility of this skin disc. Thus, the skin disc may contain one or more varieties of bacteria, the most common being *Staphylococcus epidermidis*, which has been detected in PC along with other organisms. The presence of the skin disc in PC is a suspect source of bacterial growth during storage, and it is fear of such growth which is the principal impetus for the regulation (in the USA) which limits the storage life of platelets to five days. Removal of the skin disc by filtration at an early stage of processing is, for this reason, an important advantage as it may permit the five day regulation to be relaxed.

(f) Compared with a bedside filtration method of '548, improved recovery of platelets is obtained, i.e., recovery in excess of 98% to 99% compared with about 90 to 95% typically recovered in bedside filtration.

In a second variation of this invention, the interposed filter 14 is preferably made with smaller fiber surface area, smaller filter element flow area, higher filter element density, and reduced voids volume in relation to the first variation. The total quantity of fiber used is also reduced such that a preferred range for the fiber surface area of the filter element is about 0.04 to about 0.3 $M^2$ and a more preferred range is about 0.06 to about 0.20 $M^2$. A preferred range for the filter element flow area is about 3 to about 8 $cm^2$, and a more preferred range is about 4 to about 6 $cm^2$. A preferred range for the relative voids volume is about 71% to about 83% (corresponding for PBT fibers to a density of about 0.23 to about 0.40 g/cc), and a more preferred range is from about 73% to about 80% (about 0.27 to about 0.37 g/cc). A preferred range for the CWST of the fiber is about 70 to about 115 dynes/cm, a more preferred range is about 90 to about 100 dynes/cm, and a still more preferred range is about 93 to about 97 dynes/cm. Because of its very small size, a preferred device in accordance with the second variation of the invention retains internally only 0.5 to 1 cc of PRP, representing less than a 0.5% loss of platelets.

This second variation may also comprise a porous medium wherein the upstream portion of the medium is of a higher density than the downstream portion. For example, the porous medium may comprise a higher density upstream layer for blocking the passage of red blood cells and a lower density downstream layer for the depletion of leucocytes.

Filters made in accordance with this second variation and which are interposed between the blood collection bag and PRP bag will generally remove about 85 to 99% or more of the incident leucocytes, a removal rate that is not sufficient to consistently achieve a residual leucocyte count of less than $10^7$ leucocytes per 50 ml of PC (see Table II). A principal function of this device, however, is to act as an automatic "valve" during the decantation process by instantly stopping the flow of PRP at the moment that red cells contact the filter surface. The mechanism of this valve-like action is not well understood, but it may reflect aggregation of the red cells as they reach the filter surface, forming a barrier which prevents or blocks further flow of PRP through the filter element. Aggregation of red cells on contact with the filter surface appears to be related to the CWST and/or to the surface characteristics of the fibers which are generated by the herein described procedure for modifying the fibers. This theory for the proposed mechanism is supported by the existence of filters capable of highly efficient leucocyte depletion of human red blood cell suspensions and which have pore sizes as small as 0.5 $\mu m$, through which red cells pass freely and completely with no clogging, with applied pressure of the same magnitude as that used in the present invention. On the other hand, filters of the present invention, which typically have pore diameters larger than about 0.5 $\mu m$, abruptly stop the flow of red blood cells when the filter is contacted by the red cells. This suggests that the filter's valve-like action is not related to or caused by pore size or by a filtration mechanism. The mechanism of this valve-like action is not well understood, but it may reflect zeta potential-related aggregation of the red cells as they reach the filter surface, forming a barrier which prevents or blocks further flow of PRP through the filter element.

The advantages to be gained by the use of this device include the following:

(a) The collected PRP, and the PC derived therefrom, are substantially free of red cells.

(b) The operator needs only to start the flow of PRP, which will continue to flow into the first satellite bag until red cells contact the filter surface, at which point flow stops. This eliminates the need for a skilled operator to estimate when to stop flow. The PRP so obtained has the faintly yellow color of normal PRP and, for practical purposes, may be considered to be free of red cells. The PC derived from the PRP has the characteristic light yellow color of PC and, for practical purposes, may be considered to be essentially free of red cells.

(c) The volume of PRP recovered from the blood collection bag during the plasma extraction operation is increased by about 2% to about 3% when compared with very competent manual operation and probably by about 2% to about 5% compared with average blood bank practice.

(d) Labor input is reduced, as monitoring of the interface during decantation is not required.

(e) Freshly donated blood contains platelets varying in age from newly formed to nine days or more (platelet half-life in vivo is about nine days). Newly formed platelets are larger and are generally believed to be more active. Because the younger platelets are larger, they tend to sediment faster during centrifugation and, consequently, are present in larger numbers in the PRP nearest to the red cell interface. Measurements have shown that the concentration of platelets in the 10% of the PRP volume nearest the interface is about twice that in the uppermost 10% of PRP. Taking this into account, the total number of platelets recovered is increased by about 4 to 10%.

|  | Incremental number of of platelets, % |
|---|---|
| Due to increased volume of PRP | 2 to 5 |
| Due to the higher concentration of platelets in the incremental volume of PRP | 2 to 5 |
| Total | 4 to 10% |

(f) The larger proportion of younger platelets in the PC administered to the patient means that their life within the patient after administration will be longer and that the platelets will be more active, compared with current blood bank practice.

(g) The yield of plasma, a component of value comparable with that of PRC and PC, is also increased by about 2 to about 5%.

(h) Insofar as the plasma yield is increased, the plasma content of the PRC is decreased. This is advantageous because the MHC (major histocompatibility complex) contained in the plasma is responsible for the occurrence of Urticaria (hives) in a proportion of transfusion recipients transfused with PRC.

In a third variation of this invention, the fiber is surface modified in the same manner as for the preceding versions, but the fiber surface area of the element is increased while, at the same time, the density of the filter element is somewhat reduced. In this way, the automatic blockage of flow on contact by red cells is combined with higher efficiency of leucocyte depletion.

A preferred range of fiber surface area for the third variation of the invention is from about 0.3 to about $2.0M^2$, and a more preferred range is from about 0.35 to about $0.6M^2$. The upper limits of fiber surface area reflect the desire to accomplish the filtration in a relatively short time period, and may be increased if longer filtration times are acceptable. A preferred voids volume of a filter for a filter element is in the range of about 71% to about 83% (i.e., if PBT fiber is used, corresponding to a density of the filter element in the range of about 0.24 g/cc to about 0.40 g/cc), and more preferably about 75% to about 80% (for PBT, about 0.28 g/cc to about 0.35 g/cc). A preferred filter element flow area is from about 2.5 to about 10 cm$^2$, and a more preferred area is from about 3 to about 6 cm$^2$. Leucocyte depletion efficiencies in excess of about 99.9 to about 99.99%, which corresponds to an average residual leucocyte content per unit of less than about $0.005 \times 10^7$, can be obtained.

For all three of the above described variations of the porous medium for use with PRP, a preferred range for the CWST of the fiber is preferably above about 70 dynes/cm, typically about 70 to 115 dynes/cm; a more preferred range is 90 to 100 dynes/cm, and a still more preferred range is 93 to 97 dynes/cm. A preferred range for the zeta potential (at the pH of plasma (7.3)) is about $-3$ to about $-30$ millivolts, a more preferred range is about $-7$ to about $-20$ millivolts, and a still more preferred range is about $-10$ to about $-14$ millivolts.

Housings for the leucocyte depletion media of the invention can be fabricated from any suitably impervious material, including an impervious thermoplastic material. For example, the housing may preferably be fabricated by injection molding from a transparent or translucent polymer, such as an acrylic, polystyrene, or polycarbonate resin. Not only is such a housing easily and economically fabricated, but it also allows observation of the passage of the fluid through the housing.

The housing into which the porous medium is sealed or interference fit is designed to achieve convenience of use, rapid priming, and efficient air clearance.

The blood collection and processing assembly 10, with one or more satellite bags attached or connected via a conduit, may be used integrally to separate components from whole blood. During the centrifugation step in which the red cells are concentrated at the bottom of collection bag 11, forces of up to about 5000 times gravity (5000 G) or more may be generated. Therefore, collection bag 11 is preferably flexible, as are the other bags, allowing them to settle to the bottom and against the walls of a centrifuge bucket, so that the bags themselves are subject to little or no stress.

Definitions

The following definitions are used in reference to the invention:

A) Blood Product: anti-coagulated whole blood (AWB); packed red cells obtained from AWB; platelet-rich plasma (PRP) obtained from AWB; platelet concentrate (PC) obtained from AWB or PRP; plasma obtained from AWB or PRP; red cells separated from plasma and resuspended in physiological fluid; and platelets separated from plasma and resuspended in physiological fluid. As used herein, blood component or product refers to the components described above, and to similar blood products obtained by other means and with similar properties. In accordance with the invention, each of these blood products is processed in the manner described herein.

B) Unit of Whole Blood: blood banks in the United States commonly draw about 450 milliliters (ml) of blood from the donor into a bag which contains an anticoagulant to prevent the blood from clotting. However, the amount drawn differs from patient to patient and donation to donation. Herein the quantity drawn during such a donation is defined as a unit of whole blood.

C) Unit of Packed Red Cells (PRC), Platelet-rich Plasma (PRP), or Platelet Concentrate (PC): As used herein, a "unit" is defined by the United States' practice, and a unit of PRC, PRP, PC, or of red cells or platelets in physiological fluid or plasma, is the quantity derived from one unit of whole blood. Typically, the volume of a unit varies. For example, the volume of a unit of PRC varies considerably dependent on the hematocrit (percent by volume of red cells) of the drawn whole blood, which is usually in the range of about 37% to about 54%. The concomitant hematocrit cf PRC, which varies over the range from about 50 to over 80%, depends in part on whether the yield of one or another blood product is to be minimized. Most PRC units are in the range of about 170 to about 350 ml, but variation below and above these figures is not uncommon.

D) Porous medium: refers to the porous medium through which one or more blood components pass. The platelet or PRP porous medium refers generically to any one of the media which deplete leucocytes from the non-PRC blood components, i.e., from PRP or from PC. The red cell barrier medium blocks the passage of red cells and depletes leucocytes from PRP to a greater or lesser degree while allowing the passage of platelets.

The porous medium for use with PRP may be formed from any natural or synthetic fiber or other porous material compatible with blood. Preferably, the CWST and zeta potential of the porous medium are within certain ranges, as disclosed above and as dictated by its intended use. For example, the CWST of a PRP porous medium is typically above about 70 dynes/cm.

The porous media according to the invention may be connected to a conduit interposed between the containers, and may be positioned in a housing which in turn can be connected to the conduit. As used herein, filter assembly refers to the porous medium positioned in a suitable housing. Preferably, the porous medium forms an interference fit at its edges when assembled into the housing.

The porous medium may be configured as a flat sheet, a corrugated sheet, a web, or a membrane, although it is not intended that the invention should be limited thereby.

E) Voids volume is the total volume of all of the pores within a porous medium. Voids volume is expressed hereinafter as a percentage of the apparent volume of the porous medium.

F) Conversion of density when using fibers other than PBT: In the preceding exposition the term density has been used, and the density values quoted for the filter element have been based on the use of PBT fibers. Other fibers which differ in density from the PBT may be used, as noted above, providing that their surfaces have, or have been modified to have, the characteristics noted above, e.g., a CWST of greater than 70 dynes/cm. In accordance with the invention, to use an alternate fiber of different density, the density of an element made using an alternate fiber may be calculated as follows:

Denoting V as a percentage of the voids volume relative to the apparent volume of the PBT element [i.e., V=(volume of voids/volume of element)×100], the objective is to calculate the element density of an alternate fiber element which will have a relative voids volume percentage equal to V.

If F is the density of the alternate fiber and 1.38 g/cc is taken as the density of PBT fiber, and $M_1$ is the element density of the PBT element and $M_2$ is the density required for an element with equivalent performance, then voids volume V of the PBT fiber element is $$V = (1 - M_1/1.38) \times 100$$

and the density required for the element made using the alternate fiber is $$M_2 = F(1 - V/100).$$

The more preferred fiber diameter range for the practice of this invention is about 2 to 3 μm, the diameter being defined in terms of surface area, as described in U.S. Pat. No. 4,880,548. This range is preferred because much above this range, the dimensions of the elements and consequently the liquid hold-up volumes of the filters become significantly larger; below this range, the filter elements become relatively less coherent and are more easily compressed. For example, an element made using less than 2 μm polypropylene fibers would be compressed by the pressure developed by the plasma extractor, which can be as high as 300 mm of Hg.

Pore diameters of filter elements in accordance with the invention can be determined using the modified OSU F2 method as described in U.S. Pat. No. 4,925,572.

G) In accordance with the invention, a useful technique for the measurement of fiber surface area, for example by nitrogen gas adsorption, is that developed by Brunauer, Emmet, and Teller in the 1930's, often referred to as the "BET" measurement. Using PBT as an example, the surface area of melt blown webs can be used to calculate average fiber diameter:

$$\text{Total volume of fiber in 1 gram} = \frac{1}{1.38} \text{ cc}$$

(where 1.38=fiber density of PBT, g/cc) hence $$\frac{\pi d^2 L}{4} = \frac{1}{1.38} \tag{1}$$

Area of the fiber is $$\pi d L = A_f \tag{2}$$

Dividing (1) by (2), $$\frac{d}{4} = \frac{1}{1.38 A_f} \text{ and } d = \frac{4}{1.38 A_f} = \frac{2.9}{A_f},$$

or $(0.345 A_f)^{-1}$ where
  L=total length in cm of 1 gram of fiber,
  d=average fiber diameter in centimeters, and
  $A_f$=fiber surface area in cm$^2$/g.
If the units of d are micrometers, the units of $A_f$ become M$^2$/g (square meters/gram), which will be used hereinafter. For fibers other than PBT, substitute the density for 1.38.

H) General procedure for measuring zeta potential: Zeta potential was measured using a sample cut from a ⅛ inch thick stack of webs.

The zeta potential was measured by placing the sample in an acrylic filter holder which held the sample snugly between two platinum wire screens 100×100 mesh (i.e., 100 wires in each direction per inch). The meshes were connected, using copper wire, to the terminals of a Triplett Corporation model 3360 Volt-Ohm Meter, the mesh on the upstream side of the sample being connected to the positive terminal of the meter. A pH-buffered solution was flowed through the sample using a differential pressure of 45 inches of water column across the filter holder and the effluent was collected. For measurements at pH 7, a buffered solution was made by adding 6 ml pH 7 buffer (Fisher Scientific Co. catalog number SB108-500) and 5 ml pH 7.4 buffer (Fisher Scientific Co. catalog number SB110-500) to 1 liter pyrogen-free deionized water. For measurements at pH 9, a buffered solution was made by adding 6 ml pH 9 buffer (Fisher Scientific Co. catalog number SB114-500) and 2 ml pH 10 buffer (Fisher Scientific Co. catalog number SB116-500) to 1 liter pyrogen-free deionized water. The electrical potential across the filter holder was measured during flow (it required about 30 seconds of flow for the potential to stabilize) and was corrected for cell polarization by subtracting from it the electrical potential measured when flow was stopped. During the period of flow the pH of the liquid was measured using a Cole-Parmer model J-5994-10 pH meter fitted with an in-line model J-5993-90 pH probe. The conductivity of the liquid was measured using a Cole-Parmer model J-1481-60 conductivity meter fitted with a model J-1481-66 conductivity flow cell. Then the polarity of the volt meter was reversed, and the effluent was flowed backwards through the filter holder using a differential pressure of 45 inches of water column. As in the first instance the electrical potential measured during flow was corrected for cell polarization by subtracting from it the electrical potential measured after flow was stopped. The average of the two corrected potentials was taken as the streaming potential.

The zeta potential of the medium was derived from the streaming potential using the following relationship (J. T. Davis et al., *Interfacial Phenomena*. Academic Press, New York, 1963):

$$\text{Zeta Potential} = \frac{4\pi\eta}{DP} \cdot E_S \lambda$$

where $\eta$ is the viscosity of the flowing solution, D is its dielectric constant, $\lambda$ is its conductivity, $E_S$ is the streaming potential and P is the pressure drop across the sample during the period of flow. In these tests the quantity $4\pi\eta/DP$ was equal to 0.800.

EXAMPLES

Figure 1:
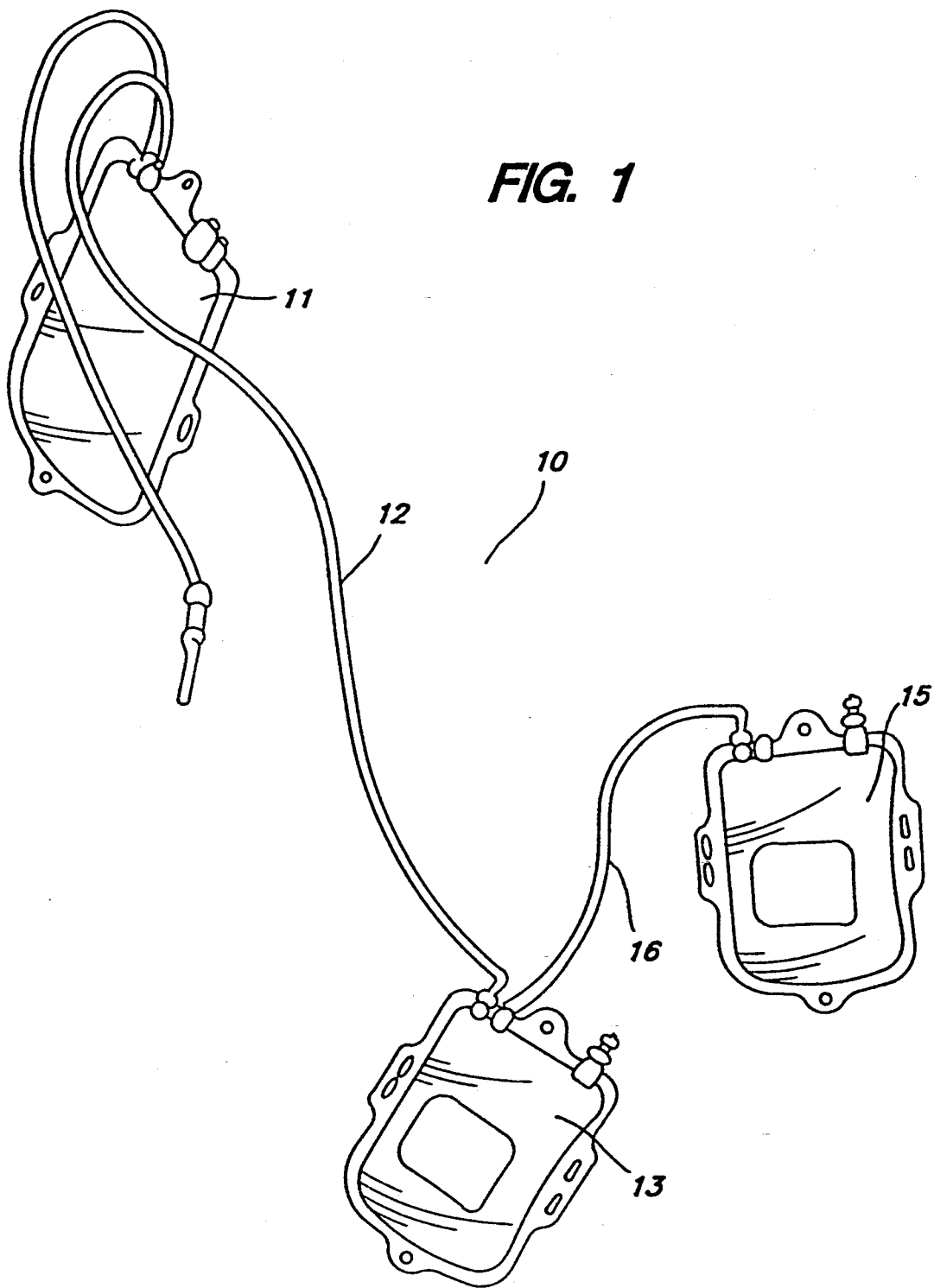
FIG. 1 is a representational view of a typical blood collection set for the collection and processing of blood. The set 10 comprises a collection bag 11 with flexible tubing 12 connected thereto and leading to a first satellite bag 13 (for PRP) and a second satellite bag 15 (for plasma) connected to the first satellite bag 13 via flexible tubing 16.

Each of the examples was run using the following basic procedure to process and test a bag of donated blood. The blood collection set was constituted as shown in FIG. 1. Bag 11, into which anticoagulant had been placed, was used to collect one unit of about 450 cc of blood from a human volunteer. Bag 11 along with its two satellite bags was then centrifuged for 5 minutes at 2280×gravity, causing the red cells to sediment into the lower parts of the bag and leave a transparent, yellowish layer of red cell-free plasma in the upper part of the bag. This bag was then transferred, with care not to disturb its contents, to a plasma extractor. With tube 12 clamped adjacent to bag 11 to prevent flow, tube 12 was cut and the test filter was inserted at position 14 in FIG. 2. With the plasma extractor applying sufficient force to the bag to generate a pressure of about 200 to 300 millimeters of mercury within the bag, the clamp on tube 12 was removed, allowing the supernatant liquid to flow through the filter into bag 13 which had been placed on a weight scale. One of several skilled operators was instructed to signal when, in normal blood bank practice, flow would have been manually shut off. For examples 1 and 2, which were in accordance with the first variation of this invention, tube 12 was at the signal promptly shut-off, the weight of PRP collected was recorded, and the contents of the bag analyzed, with results recorded in Table I.

For examples 3-8 and 9-10, the weight of the PRP bag 13 was recorded at the signal, i.e., the precise moment when flow would in normal blood bank practice have been shut off, while flow was allowed to continue until the red cell layer reached filter 14, at which time flow spontaneously and abruptly stopped, and the weight of PRP collected was recorded. The results for examples 3-8 are shown in Table II, and for examples 9 and 10 in Table III.

In each of the ten examples, the resulting PRP was visually free of red cells, and weights of the PRP were converted to volume by dividing by the density of plasma (1.04 g/cc). The data on residual leucocyte content of the PC derived from the filtered PRP are reported in Tables II and III as multiples of $10^7$ (i.e., $\times 10^7$), which can be conveniently compared with a target criterion of fewer than about $1 \times 10^7$ leucocytes per unit, which is a level believed adequate to significantly reduce alloimmunization in patients receiving platelet transfusions.

The widely used melt blowing process for making fibrous plastic webs is a convenient, economical, and effective means for manufacturing fibrous webs with fiber diameter in the 1-4 $\mu$m range. It is characteristic of this process that the quality of melt blown webs is optimal when the web weight is maintained in a preferred range of about 0.0005 to about 0.01 g/cm$^2$, and more preferably between about 0.0005 and about 0.007 g/cm$^2$. For this reason, the webs used to form the examples of this invention were, wherever necessary, formed by laying up two or more layers of web of weight about 0.006 g/cm$^2$, and then hot compressing these to form an integral filter element.

EXAMPLES 1-2

Devices were prepared in the manner of the first variation of this invention. The filter elements of these devices were preformed from 2.6 $\mu$m average diameter PBT fibers, which had been surface modified in the manner as described above and as taught in U.S. Pat. No. 4,880,548 using a mixture of hydroxyethyl methacrylate and methacrylic acid in a monomer ratio of 0.35:1 to obtain a CWST of 95 dynes/cm and a zeta potential of −11.4 millivolts. Filter element effective diameter was 4.74 cm, presenting a filter area of 17.6 cm$^2$, thickness was 0.15 cm, voids volume was 83% (density=0.23 g/cc), and fiber surface area was 0.69 M$^2$. The volume of PRP held up within the filter housing was 2.5 cc, representing a loss of PRP due to hold-up of about 1%. The results, obtained using the operating procedure described earlier in this section for the first variation, are shown in Table I.

TABLE I

| | Leucocyte Depletion Efficiency of the First Variation | | |
|---|---|---|---|
| Example Number | Volume of PRP passed, cc | Leucocyte content of PC after filtration (per unit)* | Leucocyte removal efficiency,** % |
| 1 | 237 | <.006 × 10$^7$ | >99.9% |
| 2 | 206 | <.006 × 10$^7$ | >99.9% |

*Total leucocyte count in the PC after centrifuging the filtered PRP to obtain the PC.
**Assumes that the leucocyte content of the PRP prior to filtration conformed to an average value of 5 × 10$^7$ per unit.

EXAMPLES 3-8

Devices were prepared in the manner of the second ("automatic valve") variation of this invention. The filter elements of these devices were preformed from 2.6 $\mu$m average diameter PBT fibers, which had been surface modified in the manner as described above and as taught in U.S. Pat. No. 4,880,548 using hydroxyethyl methacrylate and methacrylic acid in a monomer ratio of 0.35:1 to obtain a CWST of 95 dynes/cm and a zeta potential of −11.4 millivolts. The filter element's effective diameter was 2.31 cm, presenting a filter area of 4.2 cm$^2$, thickness was 0.051 cm, voids volume was 75% (density, 0.34 g/cc), and fiber surface area was 0.08 m$^2$.

The volume of PRP held up within the filter housing was <0.4 cc, representing a loss of PRP due to hold-up of less than 0.2%. In each test, flow stopped abruptly as red cells reached the upstream surface of the filter element, and there was no visible evidence of red cells or hemoglobin downstream. The results obtained, using the operating procedure described earlier in this section for the second variation, are shown in Table II.

TABLE II

| 1 Example Number | 2 Estimated volume/PRP using normal blood bank practice, ml | 3 Volume of PRP obtained using the procedure of invention, ml | 4 Incremental volume, percent | 5 Leucocyte content after filtration (per unit) of PC* × $10^7$ |
|---|---|---|---|---|
| 3 | 175.2 | 178.8 | 2.0 | 1.0 |
| 4 | 212.9 | 218.8 | 2.7 | 1.7 |
| 5 | 221.1 | 225.7 | 2.0 | 0.5 |
| 6 | 185.9 | 191.4 | 2.9 | 0.2 |
| 7 | 257.2 | 263.2 | 2.3 | <0.1 |
| 8 | 196.6 | 200.7 | 2.1 | 0.1 |

*Total leucocyte count in the PC after centrifuging the filtered PRP to obtain PC.

EXAMPLES 9-10

Devices were prepared in the manner of the third variation of this invention, i.e., the combination of an automatic shut-off valve and a high efficiency filter, both comprised in a single filter. The filter elements of these devices were preformed from 2.6 μm average diameter PBT fibers, which had been surface modified in the manner as described above and as taught in U.S. Pat. No. 4,880,548 using a mixture of hydroxyethyl methacrylate and methacrylic acid in a monomer ratio of 0.35:1 to obtain a CWST of 95 dynes/cm and a zeta potential of −11.4 millivolts at the pH of plasma (7.3). The filter element effective diameter was 2.31 cm presenting a filter area of 4.2 cm² thickness was 0.305 cm, density was 0.31 g/cc (voids volume=77.5%), and fiber surface area was 0.46 M². The volume of PRP held up within the filter housing was 1.3 cc, representing a loss of PRP due to hold up within the filter of about 0.5%. In each case, flow stopped abruptly as red cells reached the upstream surface of the filter element, and there was no visible evidence of red cells or hemoglobin downstream. The results obtained, using the operating procedure described earlier in this section for the third variation, are shown in Table III.

intention is to cover all modifications, equivalents, and alternatives falling within the spirit and scope of the invention.

We claim:

1. A device for the collection and processing of a blood product comprising a first container and at least one second container connected thereto, wherein a porous medium barring passage of red blood cells is interposed between the first container and the second container, the porous medium permitting platelets to pass therethrough until red blood cells block the porous medium.

2. The device of claim 1 wherein the fibers of the porous medium have been modified to present hydroxyl groups and carboxyl groups.

3. The device of claim 2 wherein an acid/acrylate monomer weight ratio in the modifying mixture used to provide hydroxyl groups and carboxyl groups is between about 0.01:1 and about 0.5:1.

4. The device of claim 3 wherein the CWST of the fibers is at least about 70 dynes/cm.

5. The device of claim 1 wherein the porous medium comprises polybutylene terephthalate fibers.

6. A filter element for processing a blood product comprising a porous, fibrous medium which removes leucocytes and permits platelets suspended in plasma to pass therethrough until red blood cells block the fibrous medium.

7. The filter element of claim 6 wherein said fibrous medium has a CWST of at least about 70 dynes/cm.

TABLE III

| | Incremental Volume and Leucocyte Depletion Efficiency of the Third Variation | | | | |
|---|---|---|---|---|---|
| Example Number | Estimated volume/PRP using normal blood bank practice, ml | Volume of PRP obtained using the procedure of invention, ml | Incremental volume, % | Leucocyte content after filtration (per unit) of PC* × $10^7$ | Leucocyte removal efficiency** |
| 9 | 251 | 256 | 2 | <0.004 | >99.9% |
| 10 | 212 | 216 | 1.9 | .005 | >99.9% |

*Total leucocyte count in the PC after centrifuging the filtered PRP to obtain PC.
**Assumes that the leucocyte content of the PRP prior to filtration conformed to an average value of 5 × $10^7$ per unit.

While the invention has been described in some detail by way of illustration and example, it should be understood that the invention is susceptible to various modifications and alternative forms, and is not restricted to the specific embodiments set forth in the Examples. It should also be understood that these Examples are not intended to limit the invention but, on the contrary, the 8. The filter element of claim 6 wherein the fibrous medium comprises polybutylene terephthalate fibers.

9. A device comprising a housing and means disposed within the housing for permitting platelets suspended in plasma to flow therethrough until red blood cells block the means.

* * * * *